US010120982B2

United States Patent
Jordan et al.

(10) Patent No.: US 10,120,982 B2
(45) Date of Patent: *Nov. 6, 2018

(54) METHOD, APPARATUS, AND COMPUTER PROGRAM PRODUCT FOR REPLENISHMENT OF ARTICLES IN A DISPENSING SYSTEM

(71) Applicant: MCKESSON CORPORATION, San Francisco, CA (US)

(72) Inventors: Michael Lee Jordan, Alpharetta, GA (US); Mike Barniskis, West Chester, PA (US); Merle Hertzler, West Chester, PA (US); Jason Warner, Downingtown, PA (US)

(73) Assignee: McKesson Corporation, San Francisco, CA (US)

( * ) Notice: Subject to any disclaimer, the term of this patent is extended or adjusted under 35 U.S.C. 154(b) by 11 days.

This patent is subject to a terminal disclaimer.

(21) Appl. No.: 15/684,729

(22) Filed: Aug. 23, 2017

(65) Prior Publication Data
US 2017/0372036 A1    Dec. 28, 2017

Related U.S. Application Data

(63) Continuation of application No. 13/528,569, filed on Jun. 20, 2012, now Pat. No. 9,779,217.
(Continued)

(51) Int. Cl.
*H04N 7/18* (2006.01)
*G06F 19/00* (2018.01)
(Continued)

(52) U.S. Cl.
CPC .......... *G06F 19/3462* (2013.01); *G06F 19/00* (2013.01); *G06Q 10/087* (2013.01);
(Continued)

(58) Field of Classification Search
CPC ... G06F 19/3462; G06Q 10/087; G07F 9/026; G07F 11/002; G07F 17/0092; H04N 7/183
(Continued)

(56) References Cited

U.S. PATENT DOCUMENTS

| 5,660,305 A | 8/1997 | Lasher et al. |
| 5,720,154 A | 2/1998 | Lasher et al. |

(Continued)

FOREIGN PATENT DOCUMENTS

| CA | 2 810 338 A1 | 9/2013 |
| WO | WO 2011/112606 A1 | 9/2011 |

OTHER PUBLICATIONS

Advisory Action for U.S. Appl. No. 13/528,569 dated Jun. 16, 2016.
(Continued)

*Primary Examiner* — Nguyen Truong
(74) *Attorney, Agent, or Firm* — Alston & Bird LLP

(57) ABSTRACT

Example embodiments of the present invention may provide an efficient method of replenishing canisters of an automated dispensing device off-line. In particular, methods may include automatically causing an image to be captured at each of two or more stages of a replenishment process, where respective images are of a loading receptacle of a replenishment station, the loading receptacle configured to hold medication. The method may also include providing for display of respective images on a device located remote from the replenishment station, and receiving an approval or rejection of at least one stage of the replenishment process in response to providing for the display of respective images.

20 Claims, 7 Drawing Sheets

Related U.S. Application Data

(60) Provisional application No. 61/661,627, filed on Jun. 19, 2012.

(51) Int. Cl.
  *G06Q 10/08* (2012.01)
  *G07F 9/02* (2006.01)
  *G07F 11/00* (2006.01)
  *G07F 17/00* (2006.01)

(52) U.S. Cl.
  CPC ............ *G07F 9/026* (2013.01); *G07F 11/002* (2013.01); *G07F 17/0092* (2013.01); *H04N 7/183* (2013.01)

(58) Field of Classification Search
  USPC ........................................................ 348/143
  See application file for complete search history.

(56) References Cited

U.S. PATENT DOCUMENTS

| | | |
|---|---|---|
| 5,771,657 A | 6/1998 | Lasher et al. |
| 6,317,648 B1 | 11/2001 | Sleep et al. |
| 6,535,637 B1 | 3/2003 | Wootton et al. |
| 6,892,512 B2 | 5/2005 | Rice et al. |
| 6,970,769 B2 | 11/2005 | Rice et al. |
| 7,894,656 B2 | 2/2011 | Kim |
| 8,141,330 B2 | 3/2012 | Henkel |
| 8,145,501 B1 | 3/2012 | Heald et al. |
| 8,775,198 B2 | 7/2014 | Wiener et al. |
| 2005/0171813 A1 | 8/2005 | Jordan |
| 2009/0030722 A1 | 1/2009 | Wiener et al. |
| 2012/0330684 A1 | 12/2012 | Jacobs et al. |
| 2013/0253700 A1 | 9/2013 | Carson et al. |

OTHER PUBLICATIONS

Advisory Action for U.S. Appl. No. 13/528,569 dated Mar. 27, 2017.
Notice of Allowance for Canadian Patent Application No. 2,818,494 dated Mar. 30, 2017.
Office Action for Canadian Application No. 2,818,494 dated Apr. 9, 2015.
Office Action for Canadian Application No. 2,818,494 dated Mar. 15, 2016.
Office Action for U.S. Appl. No. 13/528,569 dated Apr. 10, 2015.
Office Action for U.S. Appl. No. 13/528,569 dated Jan. 26, 2017.
Office Action for U.S. Appl. No. 13/528,569 dated Jul. 19, 2016.
Office Action for U.S. Appl. No. 13/528,569 dated Mar. 9, 2016.
Office Action for U.S. Appl. No. 13/528,569 dated Oct. 13, 2015.
Office Action from Canadian Patent Application No. 2,818,494, dated May 12, 2014.
Office Action for U.S. Appl. No. 13/528,569 dated Jun. 15, 2017.
Notice of Allowance for U.S. Appl. No. 13/528,569 dated Aug. 2, 2017.

METHOD, APPARATUS, AND COMPUTER PROGRAM PRODUCT FOR REPLENISHMENT OF ARTICLES IN A DISPENSING SYSTEM

CROSS-REFERENCE TO RELATED APPLICATIONS

This application claims priority to U.S. patent application Ser. No. 13/528,569, filed on Jun. 20, 2012, which claims priority to Provisional Patent Application Ser. No. 61/661,627, filed on Jun. 19, 2012, the contents of each are incorporated herein by reference.

FIELD OF THE INVENTION

The present invention relates to replenishment of articles in an automated dispensing system, and more particularly to providing a method, apparatus, and computer program product for ensuring accuracy and efficiency of replenishment of medications in an automated pharmaceutical dispensing system.

BACKGROUND

Automated dispensing systems are often used to store quantities of items, often in bulk, and to dispense the items to a container or user in response to an instruction to fill an order. Automated dispensing systems may dispense various articles, such as medications when filling prescription orders. Automated dispensing systems provide a mechanism for accurately and repeatably filling orders in a manner that is faster and more efficient than manual methods.

The accuracy of the quantity and type of item dispensed may be of great importance, particularly when the automated dispensing system is dispensing medications. Further, the quantity of articles items dispensed may be of great importance to ensure a prescription is completely filled and costly overfills are avoided. Automated dispensing systems may provide a mechanism for ensuring the quantity and type of item dispensed is accurate; however, the dispensing system must be properly replenished with the correct items in order to maintain the accuracy of the dispensing system.

SUMMARY

Example embodiments of the present invention may provide an efficient method of replenishing canisters of an automated dispensing device off-line. In particular, methods may include automatically causing an image to be captured at each of two or more stages of a replenishment process, where respective images are of a loading receptacle of a replenishment station, the loading receptacle configured to hold medication. The method may also include providing for display of respective images on a device located remote from the replenishment station, and receiving an approval or rejection of at least one stage of the replenishment process in response to providing for the display of respective images. Automatically causing an image to be captured may include: receiving an identifier of a medication container containing medication that is to be loaded into the receptacle; causing an image to be captured of the loading receptacle in response to receiving the identifier; receiving an indication that the quantity of medication in the loading receptacle has reached a target quantity; and causing an image to be captured of the loading receptacle that includes the target quantity of medication.

According to example embodiments, the indication that the quantity of medication in the loading receptacle is the target quantity may include an approval request. The method may include providing for an approval of the approval request in response to the replenishment process being performed properly. The method may include receiving an indication that a replenishment process is ready to begin at the replenishment station. Receiving an indication that a replenishment process is ready to begin may include receiving at least one image of the replenishment station. The method of example embodiments may include verifying that the identifier of the medication container containing medication that is to be loaded into the loading receptacle corresponds with an expected medication container identifier, and providing for an alert in response to the identifier of the medication container not matching the expected identifier.

Methods of example embodiments may include providing for display of a reference image on the device, the reference image including an image of a reference medication unit. Providing for display of respective images may include providing for display of a first image to a user, the first image including a view of a loading receptacle which is empty, and providing for display of a second image to a user, the second image including a view of the loading receptacle including a plurality of medication units. Methods may include providing for display, on a device located proximate the loading receptacle and the device located remote from the replenishment station, of a medication identifier, information about the medication, and a target quantity of the medication. The method may include providing for display, on the device located remote from the replenishment station, of a video of at least a portion of the replenishment process. Methods may include providing for display, on the device located remote from the replenishment station, of an alert in response to an anomaly in the replenishment process. An audit trail of the replenishment process may be stored.

Example embodiments of the present invention may provide a computer program product including at least one non-transitory computer-readable storage medium having computer-executable program code instructions stored therein. The computer-executable program code instructions including program code instructions for causing an image to be captured at each of two or more stages of a replenishment process, where respective images are of a loading receptacle of a replenishment station, the loading receptacle configured to hold medication. The computer-executable program code instructions may further include program code instructions for providing for display of respective images on a device located remote from the replenishment station, and program code instructions for receiving an approval or rejection of at least one stage of the replenishment process in response to providing for the display of respective images.

The program code instructions for causing an image to be captured at each of two or more stages of a replenishment process may further include program code instructions for receiving an identifier of a medication container containing medication that is to be loaded into the loading receptacle, program code instructions for causing an image to be captured of the loading receptacle in response to receiving the identifier, program code instructions for receiving an indication that a quantity of medication in the loading receptacle has reached a target quantity, and program code instructions for causing an image to be captured of the loading receptacle including the target quantity of medication. The indication that the quantity of medication in the loading receptacle has reached the target quantity may include an approval request. The computer program product may further include program code instructions for receiving an indication that the replenishment process is ready to begin at the replenishment station. The computer program product may include program code instructions for verifying that the identifier of the medication container containing medication that is to be loaded into the loading receptacle corresponds with an expected identifier, and program code instructions for providing for an alert in response to the identifier of the medication container not matching the expected identifier.

Example embodiments of the present invention may provide a method including capturing an image of a loading receptacle of a replenishment station in response to receiving an indication that a medication container has been identified as correct, and providing for sending the image of the loading receptacle to a device located remotely from the replenishment station for approval in response to capturing the image. The indication that a medication container has been identified as correct may be provided in response to reading an identifier of the medication container and verifying that the identifier of the medication container matches an expected identifier.

BRIEF DESCRIPTION OF THE SEVERAL VIEWS OF THE DRAWINGS

Reference will now be made to the accompanying drawings, which are not necessarily drawn to scale, and wherein.

DETAILED DESCRIPTION

Figure 1:
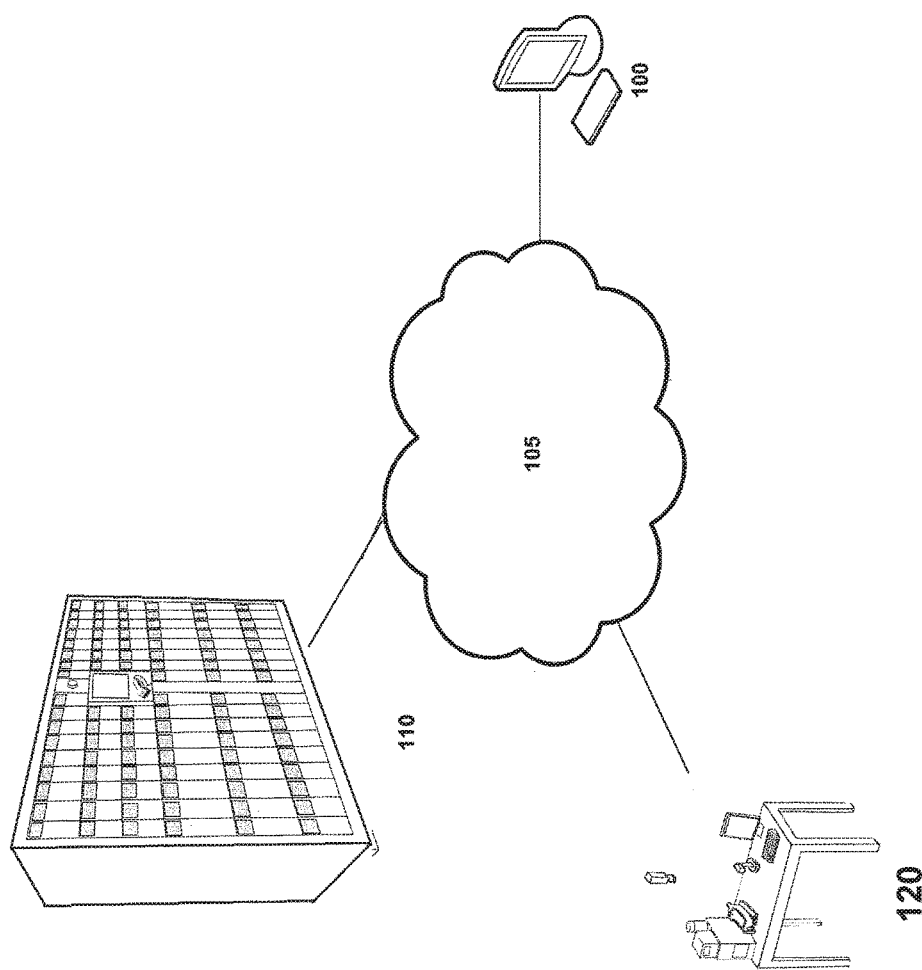
FIG. 1 illustrates a system that can be used in conjunction with various embodiments of the present invention.

Embodiments of the present invention now will be described more fully hereinafter with reference to the accompanying drawings, in which some, but not all embodiments of the invention are shown. Indeed, the invention may be embodied in many different forms and should not be construed as limited to the embodiments set forth herein; rather, these embodiments are provided so that this disclosure will satisfy applicable legal requirements. Like numbers refer to like elements throughout. The terms top, bottom, side, up, down, upwards, downwards, vertical, horizontal, and the like as used below do not imply a required limitation in all embodiments of the present invention but rather are used herein to help describe relative direction or orientation in exemplary embodiments illustrated in the figures.

As should be appreciated, various embodiments may be implemented in various ways, including as methods, apparatus, systems, or computer program products. Accordingly, various embodiments may take the form of an entirely hardware embodiment or an embodiment in which a processor is programmed to perform certain steps. Furthermore, various implementations may take the form of a computer program product on a computer-readable storage medium having computer-readable program instructions embodied in the storage medium. Any suitable computer-readable storage medium may be utilized including hard disks, CD-ROMs, optical storage devices, or magnetic storage devices.

Various embodiments are described below with reference to block diagrams and flowchart illustrations of methods, apparatus, systems, and computer program products. It should be understood that each block of the block diagrams and flowchart illustrations, respectively, may be implemented in part by computer program instructions, e.g., as logical steps or operations executing on a processor in a computing system. These computer program instructions may be loaded onto a computer, such as a special purpose computer or other programmable data processing apparatus to produce a specifically-configured machine, such that the instructions which execute on the computer or other programmable data processing apparatus implement the functions specified in the flowchart block or blocks.

These computer program instructions may also be stored in a computer-readable memory that can direct a computer or other programmable data processing apparatus to function in a particular manner, such that the instructions stored in the computer-readable memory produce an article of manufacture including computer-readable instructions for implementing the functionality specified in the flowchart block or blocks. The computer program instructions may also be loaded onto a computer or other programmable data processing apparatus to cause a series of operational steps to be performed on the computer or other programmable apparatus to produce a computer-implemented process such that the instructions that execute on the computer or other programmable apparatus provide operations for implementing the functions specified in the flowchart block or blocks.

Accordingly, blocks of the block diagrams and flowchart illustrations support various combinations for performing the specified functions, combinations of operations for performing the specified functions, and program instructions for performing the specified functions. It should also be understood that each block of the block diagrams and flowchart illustrations, and combinations of blocks in the block diagrams and flowchart illustrations, can be implemented by special purpose hardware-based computer systems that perform the specified functions or operations, or combinations of special purpose hardware and computer instructions.

FIG. 1 provides an illustration of a system that can be used in conjunction with various embodiments of the present invention. As shown in FIG. 1, an example embodiment of the system may include an automated dispensing system 110, one or more networks 105, a replenishment station 120, and an approval station 100. Embodiments may include other network entities from which data may be received from or transmitted to, as will be described further below. Each of the components of the system may be in electronic communication with, for example, one another over the same or different wireless or wired networks (e.g., network 105) including, for example, a wired or wireless Personal Area Network (PAN), Local Area Network (LAN), Metropolitan Area Network (MAN), Wide Area Network (WAN), or the like. Additionally, while FIG. 1 illustrates the various system entities as separate, standalone entities, the various embodiments are not limited to this particular architecture. Further, while the illustrated embodiment of FIG. 1 depicts an approval station 100 that is separate from the replenishment station 120, example embodiments may include where the replenishment station and approval station are a single station.

Figure 2:
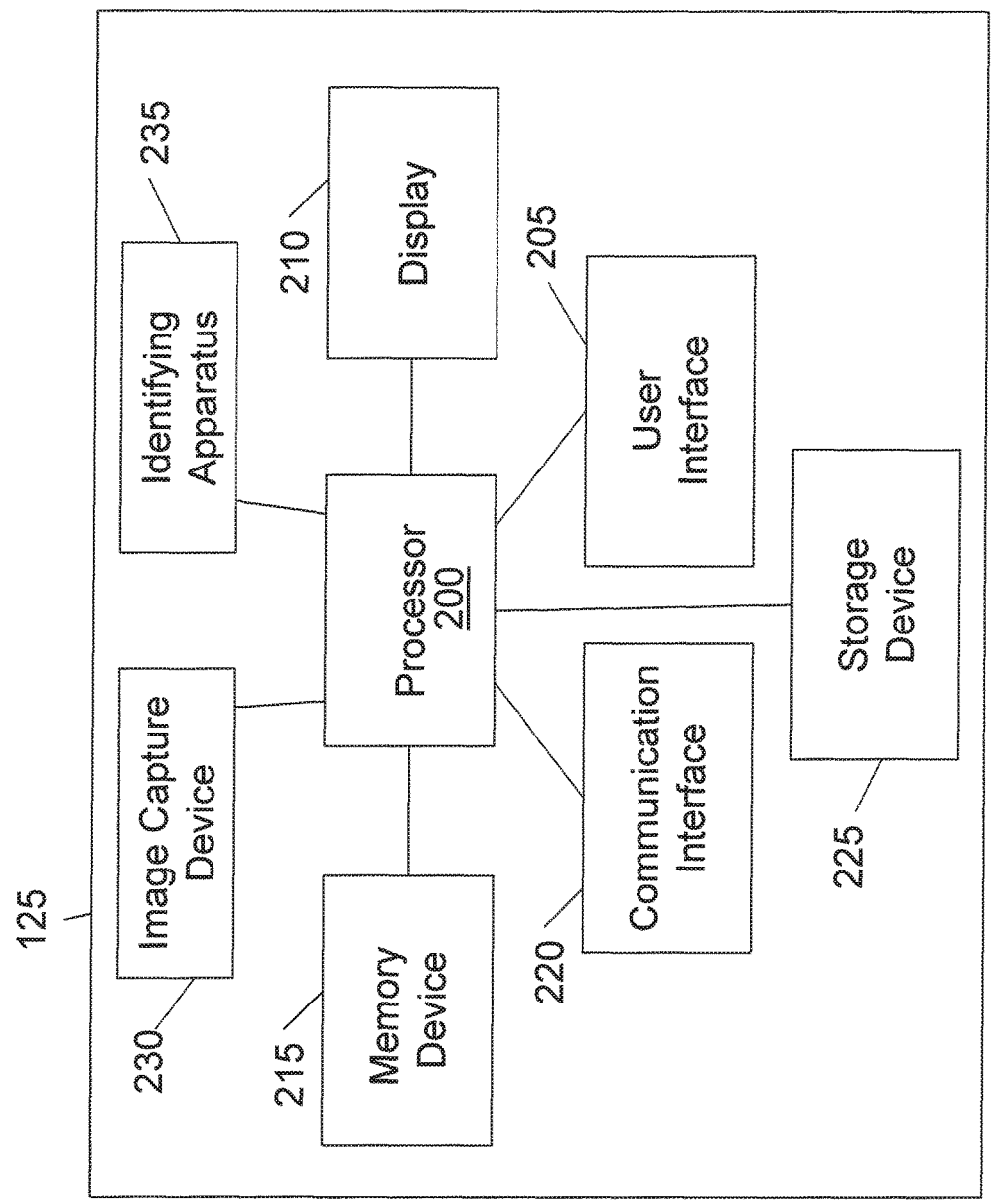
FIG. 2 illustrates a schematic diagram of an replenishment station controller according to an example embodiment of the present invention.

Example embodiments of the replenishment station 120 as described herein may include a controller configured to control or otherwise monitor and facilitate activities performed at the replenishment station 120. FIG. 2 provides a schematic of an example embodiment of a controller 125 of a replenishment station 120. In general, the term "controller" may refer to, for example, any computer, computing device, mobile phone, desktop, tablet, notebook or laptop, distributed system, server, blade, gateway, switch, processing device, or combination of processing devices adapted to perform the functions described herein. The replenishment station controller 125 may include, be associated with, or be in communication with a variety of computing entities, such as pharmacy inventory management systems, medication dispensing units, data storage/facilitation computing entities, or other devices that may interface with inventory management, dispensing, replenishing, etc. While example embodiments of automated dispensing systems may be implemented in virtually any setting which may benefit from automated dispensing of articles, embodiments described herein will be described generally with respect to the field of healthcare in which medications, medical devices, and other articles may be dispensed for patients or caregivers. However, it is appreciated that embodiments of the present invention may apply to various other embodiments of automated dispensing systems and devices.

As will be understood from FIG. 2, in one embodiment, the replenishment station controller 125 may include a processor 200 that communicates with other elements of the replenishment station controller 125 via a system interface or bus. The processor 200 may be embodied in a number of different ways. For example, the processor 200 may be embodied as a processing element, processing circuitry, a coprocessor, a controller or various other processing devices including integrated circuits such as, for example, an application specific integrated circuit (ASIC), a field programmable gate array (FPGA), a hardware accelerator, and/or the like.

In an exemplary embodiment, the processor 200 may be configured to execute instructions stored in memory or otherwise accessible to the processor 200. As such, whether configured by hardware or software methods, or by a combination thereof, the processor 200 may represent an entity capable of performing operations according to embodiments of the present invention when configured accordingly. For example, as discussed in more detail below, the replenishment station controller 125 may be configured, among other things, to facilitate accurate replenishment of canisters from an automated dispensing system. The replenishment station controller 125 may also be used to create an audit trail for the replenishment of articles for an automated dispensing system and provide a mechanism for approvals or certification of various steps of the replenishment process. A user interface 205 may be configured for user input to initiate the replenishment process or to confirm, advance, or otherwise interact with operations of the replenishment process. The user interface 205 may include a keyboard, a pointing device, or other mechanism for a user to communicate with the processor 200 and interact with the replenishment station controller 125.

Replenishment station controllers according to example embodiments may further include a display 210 which may be configured to present information to a user pertaining to the replenishment process and to communicate alerts or confirm success of various steps of the replenishment process. The display 210 may also be configured to present information to a user pertaining to the status of the replenishment station, information regarding inventory, or any information which may be useful to a user of the device. The display 210 may include a touch screen display which may partially or fully comprise the user interface 205. As noted above, example embodiments may include a replenishment station that also incorporates the approval station. In such an embodiment, the user interface 205 and display 210 may be used for the approval process of the audit trail that is further detailed below.

The replenishment station controller 125 may further include or be in communication with an image capture device 230. The image capture device may include a still camera, a video camera, a thermal imaging camera, and/or the like. The image capture device 230 of embodiments of the present invention may be used to capture images and/or video of various stages of the replenishment process as will be further detailed below. Embodiments of the controller may further include or be in communication with an identifying apparatus 235 configured to identify an item that is to be used in the replenishment process, such as a bulk medicine container, a canister, a user, an approval authority, or the like. The identifying apparatus 235 may include an apparatus with a processor such as a barcode scanner, an image capture device configured to recognize alpha-numeric indicia or other identifying marks, an RFID reader, or the like.

The replenishment station controller 125 may further include transitory and non-transitory memory device 215, which may include both random access memory (RAM) and read only memory (ROM). The ROM may be used to store a basic input/output system (BIOS) containing the basic routines that help to transfer information to the different elements within the replenishment station controller 125.

In addition, in one embodiment, the replenishment station controller 125 may include at least one storage device 225, such as a hard disk drive, a CD drive, and/or an optical disk drive for storing information on various computer-readable media. The storage device(s) 225 and its associated computer-readable media may provide non-volatile storage. The computer-readable media described above could be replaced by any other type of computer-readable media, such as embedded or removable multimedia memory cards (MMCs), secure digital (SD) memory cards, Memory Sticks, electrically erasable programmable read-only memory (EEPROM), flash memory, hard disk, and/or the like. The storage device may be configured to store, for example, an audit trail of operations, errors, alerts, and approvals of a replenishment process together with an identifier of the user and/or the approving authority responsible for a respective replenishment process.

Furthermore, a number of executable instructions, applications, scripts, program modules, and/or the like may be stored by the various storage devices 225 and/or within memory device 215. As discussed in more detail below, these executable instructions, applications, program modules, and/or the like may control certain aspects of the operation of the replenishment station controller 125 with the assistance of the processor 200 and operating system, although their functionality need not be modularized. In addition to the program modules, the replenishment station controller 125 may store or be in communication with one or more databases.

Also located within the replenishment station controller 125, in one embodiment, is a communication interface 220 for interfacing with various computing entities. This communication may be via the same or different wired or wireless networks (or a combination of wired and wireless networks). For instance, the communication may be executed using a wired data transmission protocol, such as fiber distributed data interface (FDDI), digital subscriber line (DSL), Ethernet, asynchronous transfer mode (ATM), frame relay, data over cable service interface specification (DOCSIS), or any other wired transmission protocol. Similarly, the automated storage device controller 100 may be configured to communicate via wireless external communication networks using any of a variety of protocols, such as 802.11, general packet radio service (GPRS), Universal Mobile Telecommunications System (UMTS), Code Division Multiple Access 2000 (CDMA2000), CDMA2000 1× (1×RTT), Wideband Code Division Multiple Access (WCDMA), Time Division-Synchronous Code Division Multiple Access (TD-SCDMA), Long Term Evolution (LTE), Evolved Universal Terrestrial Radio Access Network (E-UTRAN), Evolution-Data Optimized (EVDO), High Speed Packet Access (HSPA), High-Speed Downlink Packet Access (HSDPA), IEEE 802.11 (Wi-Fi), 802.16 (WiMAX), ultra wideband (UWB), infrared (IR) protocols, Bluetooth™ protocols, wireless universal serial bus (USB) protocols, and/or any other wireless protocol.

It will be appreciated that one or more of the replenishment station controller's 125 components may be located remotely from other replenishment station controller components. For example the storage device 225 may be located on a remote network entity. Furthermore, one or more of the components may be combined and additional components performing functions described herein may be included in the replenishment station controller 125.

Figure 3:
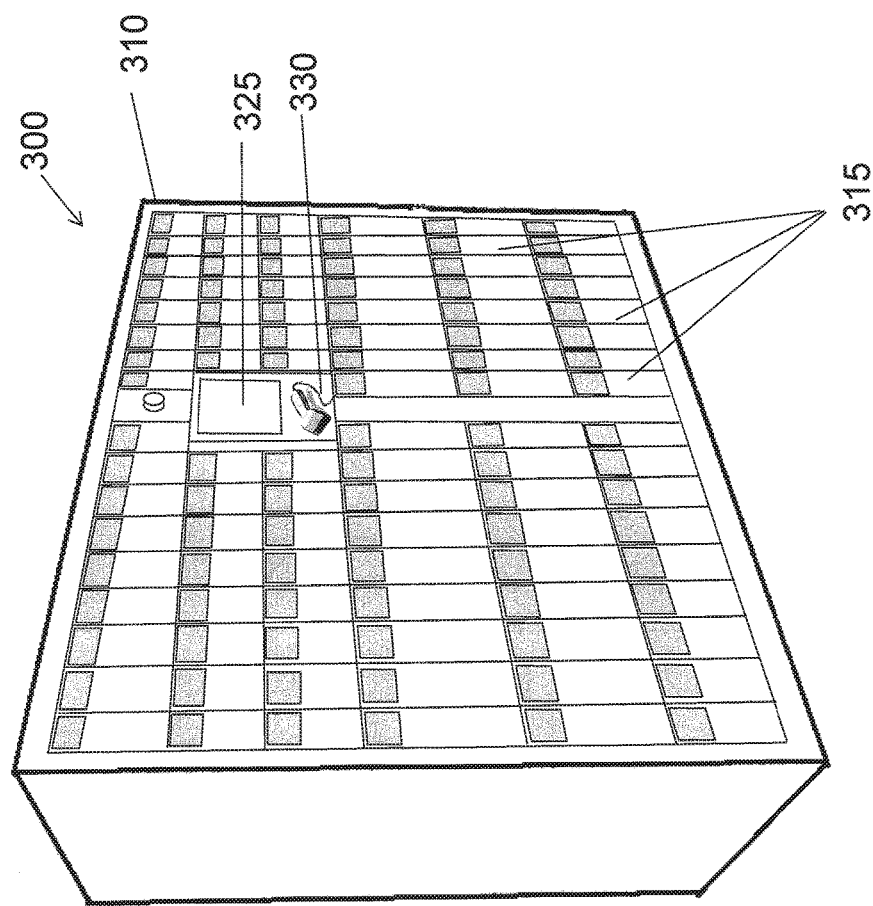
FIG. 3 illustrates an example embodiment of an automated dispensing system which may benefit from example embodiments of the present invention.

In one embodiment, an automated dispensing system may be used to hold/store/dispense various medications. Such dispensing systems may be used in a variety of environments, including retail pharmacies, central fill pharmacies, hospitals, etc. FIG. 3 illustrates an example embodiment of an automated dispensing system 300 which may be configured to automatically dispense prescribed quantities of a particular medication in response to receiving a prescription order. Automated dispensing systems 300 which may benefit from example embodiments of the present invention may include a cabinet 310 or enclosure. Within the enclosure may be a plurality of canisters 315, each configured to hold a quantity of a single medication. The automated dispensing system 300 may further include a mechanism by which medications, such as pills or capsules, are dispensed from the canisters and counted for placement into a receptacle, such as a prescription bottle. The dispensing mechanism may be separate from the canister and, therefore, count the medication as it exits the canister, or the dispensing mechanism for a medication may be incorporated into the respective canister itself.

The capacity of each canister may depend upon the size of the medication items (e.g., pills) contained therein, and the canisters may be of varying sizes to accommodate different quantities of medication. For example, more frequently dispensed medications may be stored in canisters with larger volumes and capacities, whereas less frequently dispensed medications may be stored in smaller canisters. Optionally, in order to lower inventory costs, higher cost medications may be stored in lower quantities. As will be further detailed below, a single type and dose of medication may be stored in more than one canister, particularly if the medication is dispensed frequently.

Example embodiments of automated dispensing systems 300 may include a controller or may be otherwise connected to a network from which medication orders are received. In response to receiving a medication order, the automated dispensing system may fill the medication order by dispensing the prescribed number of items (e.g., pills, capsules, etc.) from the appropriate canister 315. The automated dispensing system may include specific locations for particular medications such that a space configured to receive a canister is configured to receive a canister containing only the expected medication at that location. Optionally, the canisters may include identifying indicia such as a barcode or RFID tag or label which may identify the medication (e.g., medication type and dose) such that the automated dispensing system may detect the medication loaded at any particular location when a canister is loaded. In an example embodiment, each canister includes a microchip which is encoded with an identifier. The microchip may be read when electrical contact is made between the microchip of the canister and electrical contacts of the dispensing system or replenishment system. While an automated dispensing system may be configured to detect a medication based on identifying indicia of a canister, a user may enter the medication information at the automated dispensing system (e.g., through user interface 330 and confirmed on display 325) and a location of the canister containing said medication. Once a canister is loaded into the automated dispensing system 300, the system may dispense quantities of medication from the canister when the medication of the canister is required to fill an order.

While automated dispensing systems 300 may automatically fill prescription orders from quantities of medications stored in canisters, the canisters will require replenishment upon depletion of their contents. Such replenishment may be a time-consuming process and may require a pharmacist to perform the replenishment operation to ensure that the appropriate medication is dispensed into the canister. However, it may be desirable to provide a series of checks and balances to ensure that the appropriate medication is loaded into the appropriate canister. While a user may be capable of filling a canister properly, steps to ensure proper filling may provide an added level of confidence and increased accuracy in an industry where accuracy is of utmost importance.

In an example embodiment of the present invention, an alert may be generated, for example, by an automated dispensing system 300, when the quantity of a particular medication within a particular canister 315 falls below a threshold value. The threshold value may be user-adjustable to accommodate factors such as the cost of the medication, the frequency of use of the medication, etc. The automated dispensing system may further be configured to generate an alert when the expiration date of a particular medication of a particular canister is approaching or has past. The alert may optionally be generated a predetermined time before the expiration date of the medication in the canister, as it may be desirable that the medication have a shelf-life of, for example, six-months or more after distribution to a consumer to allow a user time to use the medication before expiration.

Upon the alert being generated, the canister requiring replenishment may be added to a queue of canisters requiring replenishment. This queue may be the queue used by an operator during a shift or during a scheduled replenishment time frame (e.g., during scheduled downtime of an automated dispensing system). Optionally, the canister requiring replenishment may be retrieved by a user in response to the alert being generated such that the canister may be replenished on an as-needed basis. The canister requiring replenishment may be identified by a location within the automated dispensing system, by a medication name, or by other identifying indicia. Whether a canister requiring replenishment is in a queue or individually noted to a user, the user may retrieve the canister from the automated dispensing system. When replenishing a plurality of canisters, a user may load the canisters requiring replenishment onto a cart for transport to a replenishment station. Optionally, a user may first fill empty canisters at a replenishment station in response to a list of canisters requiring replenishment, and bring the canisters to the automated dispensing system where replenished canisters are swapped out for empty or substantially empty canisters.

As noted above, canisters may include a unique identifier which may be used to track the location of the canister. Replenished canisters that are loaded into the automated dispensing system may be identified by a barcode scanner, RFID reader, or the like, to identify the replenished canister. A location within the automated dispensing system and/or a canister being replaced may also be identified to indicate a canister swap between a substantially empty canister and a replenished canister. The identification of a replenished canister, together with a quantity within the canister, may be transmitted to the automated dispensing system such that the dispensing system is made aware of a replenished medication.

A replenishment station may be configured to receive a canister that requires replenishment. In an example embodiment in which a canister may not be emptied of its contents prior to arrival at the replenishment station, the same medication and dose may be used to replenish the canister. In an example embodiment in which a canister may be empty, empty canisters may be replenished with the next medication type scheduled to be replenished, regardless of whether the medication type is the same. The priority of the replenishment may be determined based upon a number of factors, including the time since the alert was generated signifying that replenishment is needed for a particular medication, the frequency of use of a particular medication, whether or not the automated dispensing system includes another canister for dispensing the same medication, etc. The replenishment queue may be organized based on these or other factors as determined to be appropriate for a particular automated dispensing system.

Figure 4:
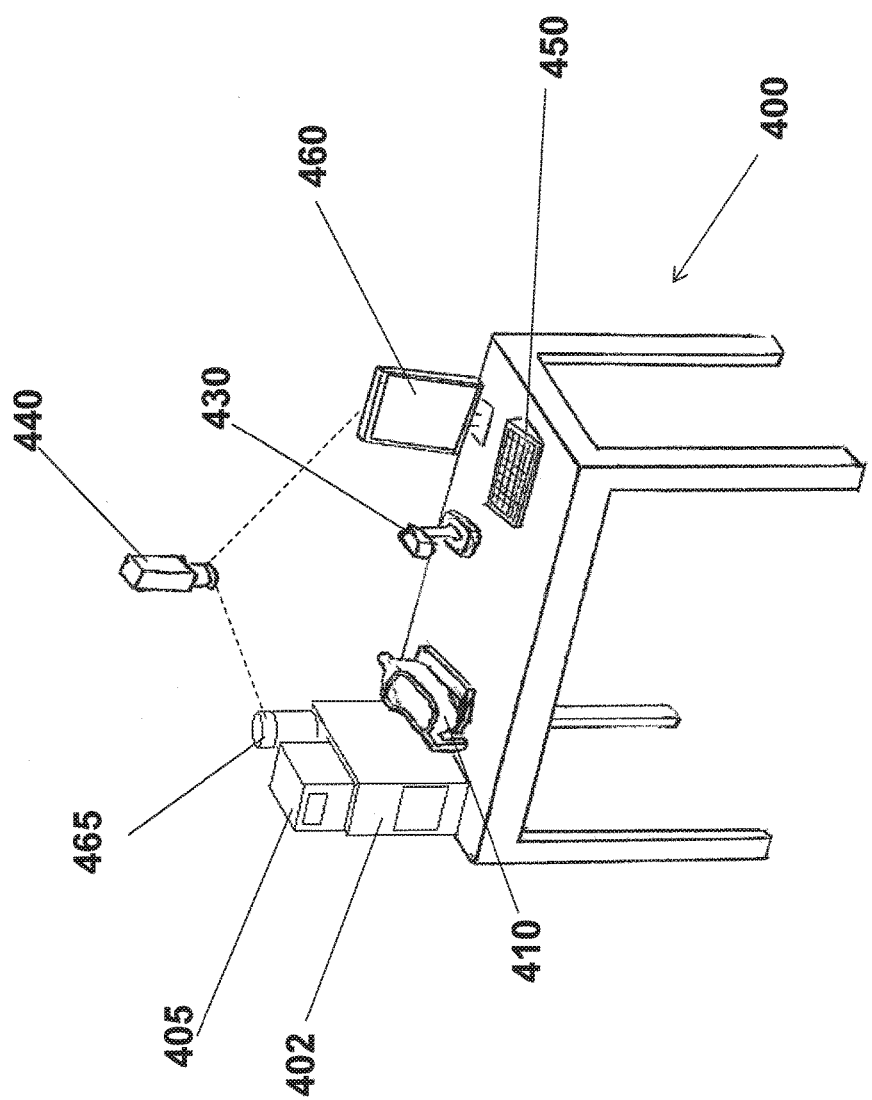
FIG. 4 illustrates an example embodiment of a replenishment station according to an example embodiment of the present invention.
Figure 5:
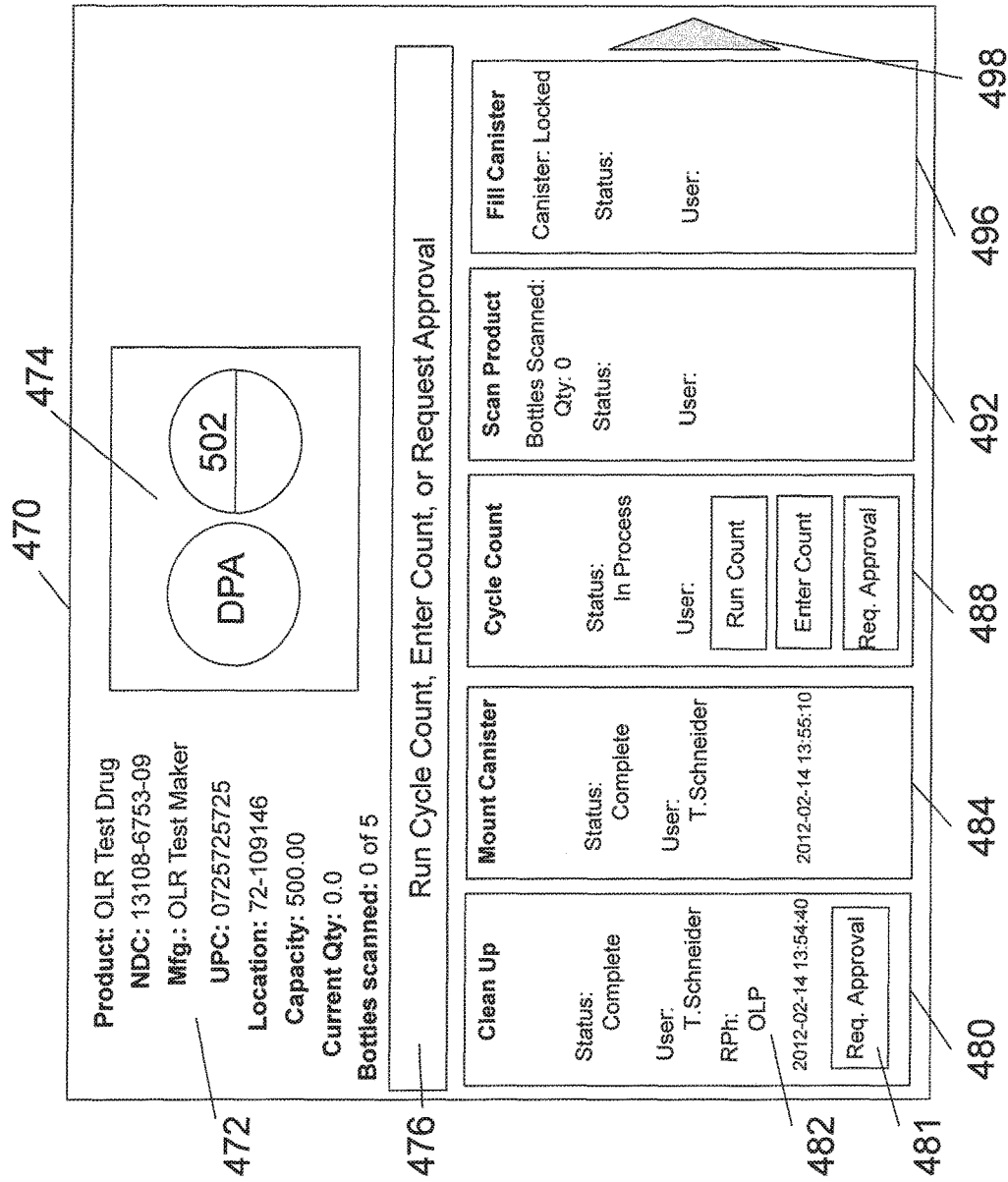
FIG. 5 is an illustration of an operator screen of a replenishment station according to an example embodiment of the present invention.

FIG. 4 illustrates an example embodiment of a replenishment station 400 which includes a calibration station 402 configured to hold the canister 405, a loading receptacle 410, a cycle count container 465, and a controller (not shown). The replenishment station may further include an identifying apparatus including a processor, such as barcode scanner 430, image capture device 440, and a user interface comprising a display 460 and a keyboard 450. The display 460 may be configured to present an operator screen 470 to a user as illustrated in FIG. 5 and detailed below with regard to the replenishment process. The controller may be co-located with the replenishment station or located remotely, communicating with the various components of the replenishment station via a network and/or wired or wireless communication protocols.

The calibration station 402 may be configured to receive the canister 405 to be replenished and control access to the canister 405. For example, the calibration station may lock and unlock the canister in response to the appropriate commands received from the replenishment station controller. Further, the calibration station may be configured to perform the cycle count as will be described further below.
The Replenishment Process The replenishment process operations may be displayed on the operator screen 470 and may progress in a logical fashion, such as from left to right or top to bottom, as the replenishment process advances. The user may be guided by the operator message instructions of the operator screen 470 and interactive features (e.g., buttons) of the operator screen 470 may become active for each operation of the process. Some operations within the replenishment process may require approval before advancing to the next operation; however, the operations requiring approval may be configured based upon the implementation of example embodiments. For example, some individual operations may require approval before a user is allowed to perform the next operation, while other operations may proceed without approval, and a review of these operations may be performed by an approving authority subsequent to their completion.

The replenishment process may begin with a particular medication requiring replenishment as requested by the automated dispensing system. An indication that the replenishment process is ready to begin may be received at the replenishment station (e.g., via the controller) and the indication may be presented on the display 460. The indication may be generated by the replenishment station in response to initiating the next replenishment process that is in a queue of medications requiring replenishment. The indication may also be generated by the automated dispensing system 300 indicating that the replenishment of a particular medication is needed. The indication may be presented to a user via the display 460 through the operator screen 470, such as by presenting information relating to the medication requiring replenishment. A medication information window 472 may identify the medication by product name, a national drug code number (NDC), the manufacturer, the universal product code (UPC), the stock location of the medication, the capacity that a canister is capable of holding of the medication, the current quantity of the medication in the dispenser (this information may be obtained during cycle count or otherwise provided by the automated dispensing system), the number of bottles required to fill the canister, and a reference image 474 of the medication. Information may further include whether restock bottles are available for using to replenish the canister, where restock bottles or containers are partially used bottles containing less than a full, new bulk container would contain.

The operator screen 470 may further include an operator message bar 476 to convey to a user the present operation and options available for completing the operation. The operator message bar may use color coding to indicate or distinguish between normal operations and alerts or warnings. The replenishment operations may be displayed within the operator display 470 as illustrated in blocks 480, 484, 488, 492, and 496.

Figure 6:
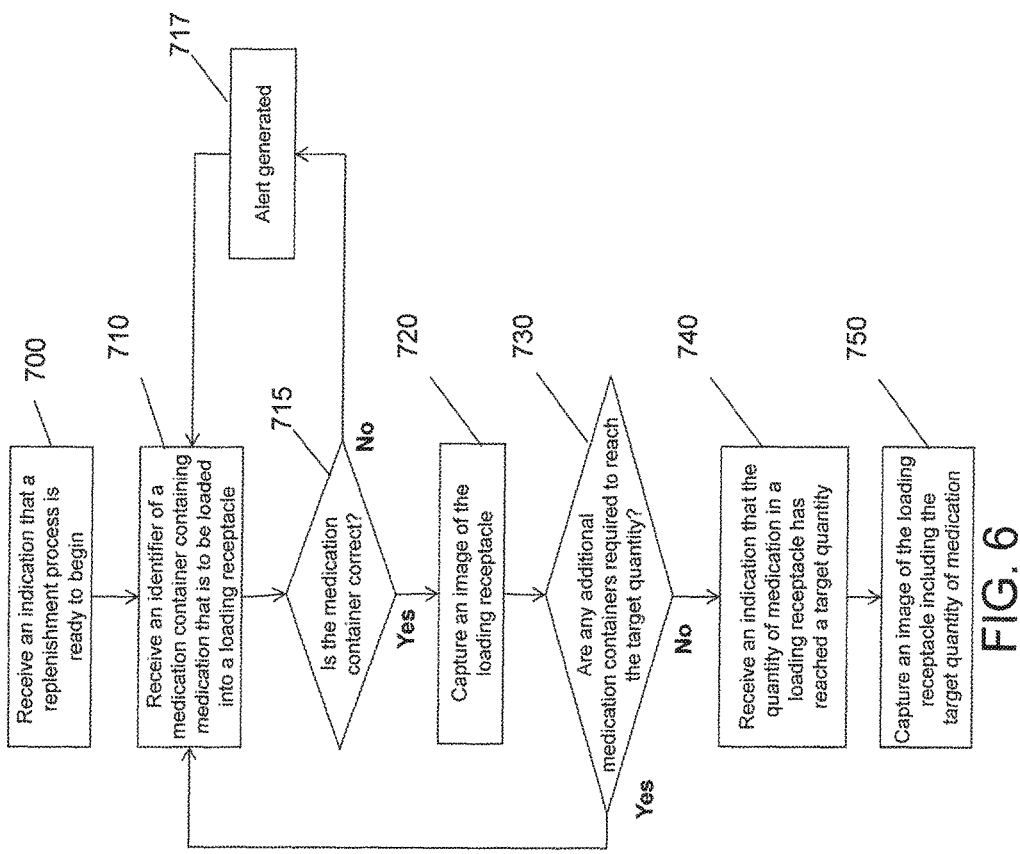
FIG. 6 is a flowchart of a method for performing operations of the replenishment process.

An example embodiment of the sequence of operations is illustrated in the flowchart of FIG. 6 and described herein with respect to the replenishment station of FIG. 4 and the operator display 470 of FIG. 5. A user may log into the replenishment station, such as logging in to controller 125 through the user interface 450/460. By logging into the replenishment station, the user is identified for purposes of creating an audit trail with respect to any canisters replenished at the replenishment station while the user is logged in. Upon logging in, an indication that a replenishment process is ready to begin may be received at operation 700. The information regarding the medication to be replenished may be displayed on display 460 as described with regard to the medication information 472 and the representative illustration of the medication 474 on the operator screen 470. The information may also display the capacity of a canister for the medication and a number of bottles or bulk containers required to reach capacity. Further, the information may include a location where the bottles of the medication may be found.

The replenishment process may begin with a user ensuring the replenishment station is clean as displayed as operation 480 on the operator screen 470. Upon ensuring the replenishment station is clean, the user may request approval from an approving authority, such as by pressing the button 481 of the operator display 470. In the illustrated embodiment of the operator display 470 of FIG. 5, approval of the cleanup operation was received by the "OLP" or "Off-Line Pharmacist" as illustrated at 482 and the operation is shown as "complete." The "cleanup" operation includes preparation of the work area of the replenishment station by ensuring that the cycle count container 465 and the loading receptacle 410 are empty and no improper medication containers are present at the replenishment station 400.

If approval is not received, the "cleanup" operation is requested again via the operator screen 470. Upon receipt of approval of the cleanup operation, the next operation may commence. The correct canister for the medication to be replenished may be retrieved. The correct canister may be retrieved from a cart or from the automated dispensing system and identified by a label including indicia which may be readable by a user and which may contain a barcode or RFID tag to be identified by the identifying apparatus 430 of the replenishment station 400. The canister may be mounted at the replenishment station in preparation for replenishing. The operator screen 470 illustrates this operation at 484. The canister may be confirmed as correct based upon the replenishment station controller recognizing the canister identification as correct. A canister that is identified as incorrect may be rejected by the replenishment station controller and the user may be instructed to retrieve the correct canister. As illustrated, the mounting of the canister may not require approval; however, in some embodiments approval may be required dependent upon the implementation. As the canister may require proper identification by the replenishment station controller, the replenishment station controller may preclude any further replenishment operations until the correct canister is identified. As such, the approving authority may not be required.

In some embodiments, the "cleanup" operation approval may be requested automatically in response to a canister being correctly identified by the identifying apparatus 430 at the replenishment station. In such an embodiment, the user may retrieve a canister, scan the canister using the identifying apparatus 430, one or more images of the replenishment station 400 may automatically be captured in response to the replenishment station controller identifying the canister, and the images and approval request may be sent for approval without requiring a user to specifically request approval.

In embodiments in which the canister from the dispensing system to be replenished may not be completely empty, a cycle count of the remaining medicine in the canister may be taken and illustrated in the operator display 470 at 488. The cycle count of the remaining medication in the canister may be taken via a measurement (e.g., weight, counter, etc.) or it may be manually counted. In an automated count, the "run count" button of operation 488 may be pressed. In the illustrated embodiment, the calibration station 402 may dispense the medication remaining in the canister 405 to the cycle count container 465 while performing the cycle count operation. The calibration station 402 may thus serve as a dispensing system for a single canister. If the user has counted the medication, the "enter count" button may be pressed to allow the user to enter the count. Upon entering the count or having the count generated (e.g., by the calibration station 402), the "request approval" button may be pressed. If there is no medication remaining in the canister, the "request approval" button may be pressed without entering a count. If the approval is not granted, the cycle count may be requested again. If the approval was received, the next operation may commence.

Upon the cycle count being complete, the replenishment station controller can identify how many units of medication are required to fill the canister, and the appropriate number of containers or bottles required to fill the canister can be indicated to a user through the medication information 472 presented on the operator display 470. In some example embodiments, the quantity to be replenished may be less than the capacity of the canister, such as when a medication is rarely used or is a high cost medication. In such embodiments, the quantity of medication required to "fill" the canister may be less than the capacity of the canister. The medication fill quantity of a canister may be user configurable such that a user is able to specify the quantity of medication for a canister to avoid, for example, dispensing jamming or canisters that are too heavy. The medication bottles or bulk containers for replenishment may be retrieved from their storage location, which may be indicated by the medication information 472. The lot number and expiration date of each medication bottle may be entered or the information may be determined in the following identification operation. Optionally, the lot number and expiration date may only be entered only when the lot and expiration date changes between containers. This avoids re-entering the same lot and expiration information while allowing the user to change the lot and expiration when necessary.

The medication containers may be identified by the identification apparatus 430 of the replenishment station 400. The medication container may include an identifier, such as a barcode or RFID tag which indicates the type of medication, the quantity, the expiration date, the lot number, etc. The identifier received by the identification apparatus 430 and/or the controller may be used to confirm that the medication container is the appropriate medication container for the ongoing replenishment process as shown in operation 710. In response to a medication container being scanned and identified as containing the proper medication, one or more images of the replenishment station may be automatically captured at operation 720. These captured images provide an audit trail that includes a visual confirmation of the contents of the loading receptacle 410 prior to the emptying of the medication container into the loading receptacle. After each medication container is identified, such as by scanning a barcode, that medication container is opened, and detrashed (i.e., any packing material and desiccants are removed), and the medication may then be emptied into the loading receptacle. The "scan product" operation 492 of the operator screen 470 may be updated as each bottle is scanned. Upon scanning of the first bottle, the number of bottles scanned would increment to one. The quantity would increment by the number of medication units from the container, and the status may read "In process."

If the medication container identified in 710 is not a correct medication container for the replenishment process, as determined at operation 715, an alert may be generated at 717. The alert may require an approving authority to override the alert to confirm that the issue has been resolved before the user is permitted to continue with the replenishment process.

After each medication container is identified as a correct medication container for the replenishment process at 715, and an image of the replenishment station is captured, the replenishment station controller 125 may determine if there are any additional medication containers needed to reach the target quantity at operation 730. If the target quantity has not yet been reached, the process may return to operation 710 where the next medication container may be identified. Upon reaching the target quantity at 730, a "Request Approval" option or button may appear or become active for a user at the "scan product" operation 492 of the operator display 470. The user may then request approval from the approval authority, such as the off-line pharmacist. An image of the replenishment station including the loading receptacle may be captured at operation 750 in response to receiving an indication that the quantity of medication in the loading receptacle has reached a target quantity at operation 740. The indication may be generated in response to the emptying of the last container being complete or in response to the user selecting a "request approval" option upon emptying the last medication container.

Errors may occur during the replenishment process described above, such as scanning an incorrect medication container, as noted above with regard to operation 715. If an incorrect medication container is scanned and identified as incorrect, an error may be presented on the display 460 and the replenishment process may be halted until an approval authority can override the error at operation 717, and assure that the appropriate medication container is retrieved. Another error which may occur includes scanning a next medication container too quickly after scanning a prior medication container. This error may be indicative of the same medication container being scanned twice, or a pouring operation not properly occurring. The minimum time between scans of medication containers may be adjustable; however, the time may be generally set to a value at which a highly-efficient operator may complete the scanning and pouring of a medication container. Another error which may occur includes scanning or identifying a medication container that would cause the quantity of medication to exceed the canister capacity. In such an example an alert may be presented to the user to not pour the contents of the medication container into the loading receptacle.

Once the target quantity of medication has been reached and an approval has been received from an approving authority, the canister may be unlocked for replenishment. A button may be presented to a user in the "Fill Canister" operation 496 of the operator screen 470. Once unlocked, the canister door may be opened and the loading receptacle 410 may be emptied into the canister 405. Upon replenishing the canister, a user may request approval at the "Fill Canister" operation 496 for the approving authority to verify the canister was properly replenished and subsequently locked. This final approval establishes that the approving authority has audited the replenishment process from beginning to end and the locked canister is asserted by the approving authority to contain the correct quantity and type of medication. The canister may then be returned to the automated dispensing system or to a cart for later loading into the automated dispensing system.

Additional replenishment operations may be required for certain medications or for certain types of canisters requiring replenishment. Example embodiments of the operator screen 470 may further include the ability to scroll to operations not presently displayed, such as by arrow 498. In such an embodiment, additional operations may be included without reducing the size of the operation windows, such as windows 488, 492, and 496.

The Approval Process

The offline replenishment station of example embodiments of the present invention allows an approving authority, such as a pharmacist, to view and approve replenishment process operations and creates an audit trail of the operations performed. The approving authority may be located proximate the replenishment station or remote from the replenishment station. The approving authority may review and approve the replenishment process from any location provided an approval station is accessible, as illustrated in the approval station 100 of FIG. 1. The approval station may include similar components as that of the replenishment station such as the processor 200, the memory device 215, the communications interface 220, the display 210, and the user interface 205 as illustrated in FIG. 2. The approval station may be adapted for an approving authority to interface with an approval screen to audit and approve various operations in the replenishment process.

Figure 7:
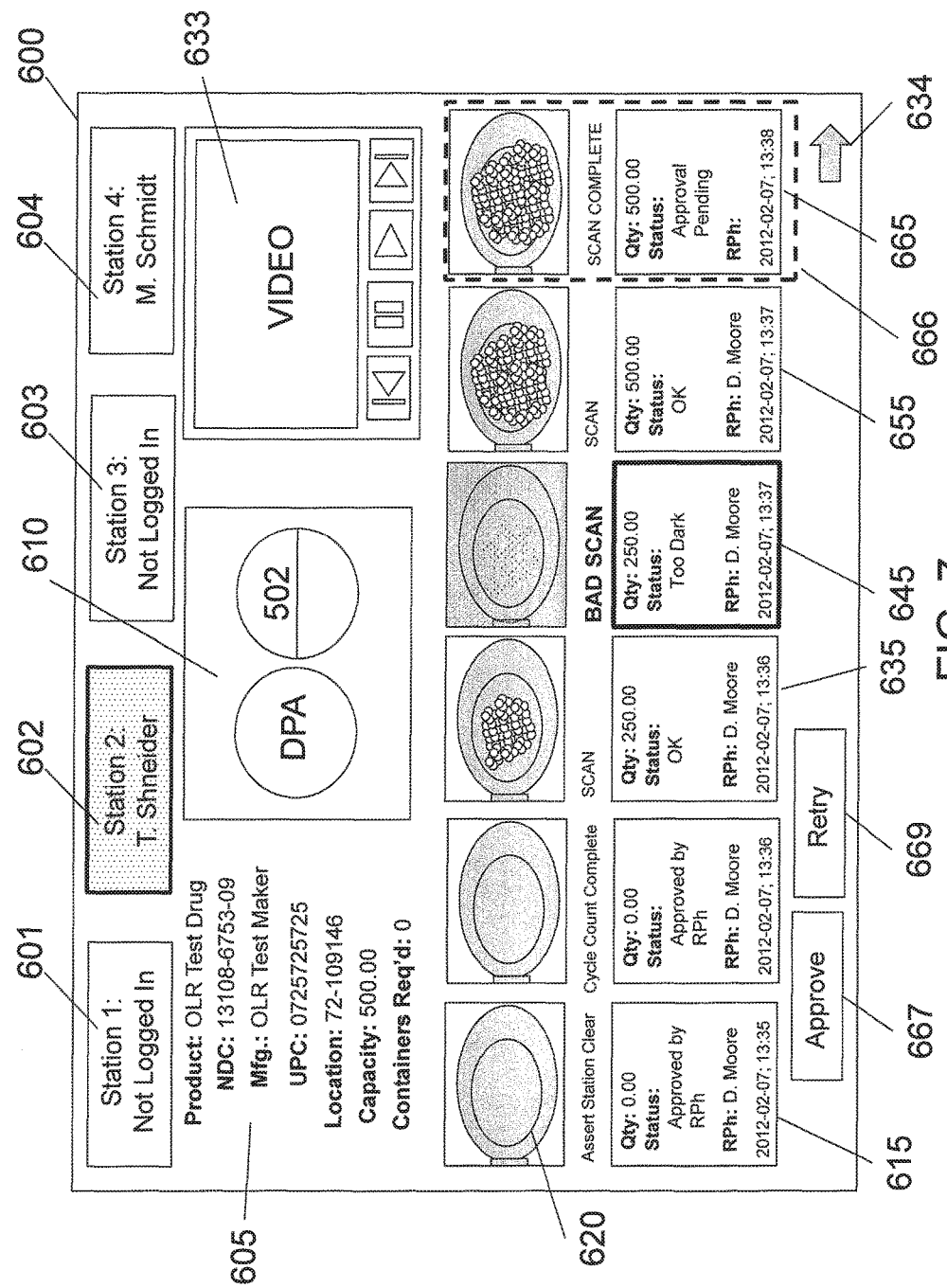
FIG. 7 is an illustration of an approver screen of an approval station according to an example embodiment of the present invention.

An example embodiment of an approver screen 600 is illustrated in FIG. 7 which includes several features common to the operator screen 470 of FIG. 5. The approver screen 600 may provide sufficient information to an approving authority such that they may provide a thorough review of each operation of the replenishment process and approve properly completed operations with confidence. In the illustrated embodiment of the approver screen 600, the information presented includes the medication information 605. The medication information may include the product name, the NDC, the UPC, the stock location, the canister capacity, etc. The approver screen may also include a reference image 610 of the medication. This reference image allows the approval authority to compare the reference image 610 to the images of medication loaded into the loading receptacle as further outlined below. The reference image 610 may allow the approving authority to see distinctive indicia, colors, shapes, etc. which may distinguish the proper medication from an improper medication.

The approver screen 600 of example embodiments may further include a video playback area 633 which may be configured to play a streaming video of the replenishment process at the replenishment station. The image capture device 440 of the replenishment station 400 of FIG. 4 may be configured to provide streaming video in addition to capturing still images of the replenishment operations. The replenishment station may further include additional video capture devices in different locations to provide multiple view points from which an approval authority may choose between when reviewing the replenishment process. In an example embodiment, the video may be paused, advanced, rewound, zoomed, or panned as desired by the approval authority to examine any feature of any replenishment operation.

Example embodiments of the approver screen 600 may include an illustration of each replenishment operation, such as cleanup operation 615, with an image 620 from the image capture device 440 of the station and the loading receptacle. The approving authority may review the cleanup operation at the approver screen 600 by viewing the image and the video 633 if desired. The operation may be selected by an approval authority, such as by touching proximate the operation on the approver screen 600 or by directing a pointing device to the operation. Upon selection of the operation, a border or other visual distinction may indicate to the user that the operation is selected, such as the border 666 around the "scan complete" operation 665. When an operation is selected, the video of that particular operation that is captured by the video or image capture device may be presented in the video playback area 633. The video segment may be limited only to the selected operation to make review of the video more efficient. In the example embodiment of the cleanup operation, the approving authority may review the image 620 and the video segment in the video playback area 633 to verify that the replenishment station is clean and the loading receptacle is empty.

Further, when an operation is selected, before the operation is approved, an "approve" button 667 and a "retry" button 669 may be presented. Optionally, the buttons presented may include a "cancel" option to exit the replenishment process. The "approve" button may be selected by an approval authority in response to verifying that the selected operation was performed properly by a user. The "retry" button 669 may be selected if the approving authority does not approve, or does not have sufficient evidence presented to them to approve the operation.

The operations presented on the approval screen 600 may include information regarding the operation, such as with the cleanup operation 615, which presents the quantity of the medication in the loading receptacle, a status (e.g., in process, approved, approval pending, etc.), and an indicator of the approval authority that has approved the operation. Further, a time-stamp of when the operation was approved may be included.

In the illustrated embodiment, the "cycle count" operation has been approved with a cycle count of zero. The "scan" operation at 635 shows a quantity of 250 units of medication and a status of "OK". The "scan" operation may be performed in response to a user scanning a bottle of medication to be emptied into the loading receptacle. The captured image for the scan operation may be reviewed by the approving authority to verify that the medication loaded into the loading receptacle matches the reference image 610. The approving authority may zoom, pan, and review the loading receptacle in more detail to ensure the medication is correct. This visual review is in addition to the replenishment station controller verifying that the medication bottle scanned is correct.

In the illustrated embodiment of FIG. 7, a "bad scan" is illustrated at 645. The bad scan may be indicative of a mis-read medication container or an improper medication container. The "bad scan" may require the approving authority to override the operation and verify that the issue that caused the bad scan has been resolved. An additional scan operation is completed at 655 showing a quantity of 500 medication units, which matches the capacity shown in the medication information 605. The status may indicate "OK" for operations that may not require approval at that particular operation, but the operations may be presented to the approving authority such that they may verify each operation before finally approving the replenishment process. Upon reaching the target capacity, the "scan complete" operation may be shown where a user has requested approval for completing the process of loading the loading receptacle. As illustrated, the status indicates "approval pending" and the "approve" button 667 and the "retry" button 669 are presented on the approver screen 600. Upon approval of the "scan complete" operation, the canister for the medication may be unlocked for replenishment by the user.

Additional operations requiring approval or review may be available to an approval authority by scrolling. An arrow or other indicator, such as arrow 634 may be presented to alert an approving authority that additional operations are disposed to the right of the illustrated operations.

Each approval authority may be able to review the replenishment process and approve the operations at multiple replenishment stations to maximize the efficiency of the approving authority. In the example approver screen 600 of FIG. 7, the approving authority may review up to four separate replenishment stations concurrently by switching between the replenishment station approver screens. Each available replenishment station may be displayed as buttons illustrated as 601, 602, 603, and 604. Each replenishment station button 601-604 may include a status, such as whether a user is logged in to the station, which may indicate that replenishment operations are occurring. The approving authority may switch between replenishment station approver screens by pressing a respective replenishment station button 601-604, either via touch screen or other pointing device. When a replenishment station is selected, such as station 2 of FIG. 7, the station button 602 may be distinguished from the other buttons 601, 603, and 604. In response to a user at a replenishment station requesting an approval or an approving authority override, the button corresponding to that replenishment station may be visually distinguished from the other buttons and may include a dynamic visual feature, such as a blinking icon, a color change, etc. Further, an audible alert may be sounded in response to an action (approval or override) requested by the approving authority for the replenishment station. In an example embodiment, the approver screen 600 may be configured to automatically switch between replenishment stations based upon a need for approval at a particular replenishment station, or if there is an issue encountered at a particular replenishment station. Such an embodiment may improve the efficiency of an approval authority by automatically displaying stations requiring action.

Example embodiments of visual distinctions of the replenishment station buttons may include distinctions that indicate a particular status of each replenishment station. For example, a dark gray color button may indicate that no user is logged in. A light gray button may indicate that a user is logged in, but no replenishment operation is in process. A green button may indicate a user is logged in, a replenishment operation is in process, and all is ok. A yellow button may indicate that an action is needed at the replenishment station, such as an approval of an operation. A red color button may indicate that there is an error at the station that needs to be resolved.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Moreover, although the foregoing descriptions and the associated drawings describe some example embodiments in the context of certain example combinations of elements and/or functions, it should be appreciated that different combinations of elements and/or functions may be provided by alternative embodiments without departing from the scope of the appended claims. In this regard, for example, different combinations of elements and/or functions than those explicitly described above are also contemplated as may be set forth in some of the appended claims. Although specific terms are employed herein, they are used in a generic and descriptive sense only and not for purposes of limitation.

That which is claimed:

1. A method of operating a replenishment station comprising:
    initiating a replenishment process wherein a medication is identified that requires replenishment;
    providing an indication of the identified medication that requires replenishment;
    receiving an identifier of a medication container containing a plurality of unit doses of a medication that is to be loaded into a loading receptacle;
    confirming that the identifier of the medication container corresponds to the identified medication, wherein an alert is generated in response to the identifier of the medication container does not correspond to the identified medication;
    receiving an indication that a quantity of dispensed medication from the medication container in the loading receptacle has reached a target quantity for dispensing;
    causing an image to be captured of the loading receptacle comprising the target quantity of medication;
    providing the captured image to a device located remotely from the replenishment station; and
    receiving an approval or rejection of the replenishment process in response to providing the captured image to a device located remotely from the replenishment station.

2. The method of claim 1, further comprising:
    providing for display of the captured image of the loading receptacle comprising the target quantity of medication;
    providing for display of a reference image comprising an image of a reference medication unit, wherein the reference image comprises one or more of a distinctive color, shape, or indicia sufficient to distinguish a proper medication from an improper medication; and
    receiving an approval or rejection of at least one stage of the replenishment process, in response to providing for the display of respective images.

3. The method of claim 1, wherein a medication is identified that requires replenishment in response to an alert indicating an available quantity of the medication is below a threshold amount.

4. The method of claim 1, wherein the identifier of a medication container containing a plurality of unit doses of a medication that is to be loaded into a receptacle is a first medication container, the method further comprising:
    receiving an identifier of a second medication container containing a plurality of unit doses of a medication that is to be loaded into a loading receptacle in response to the target quantity of medication being greater than a quantity of medication from the first medication container being less than the target quantity; and
    confirming that the identifier of the second medication container corresponds to the identified medication, wherein an alert is generated in response to the identifier of the second medication container does not correspond to the identified medication.

5. The method of claim 4, further comprising:
    capturing an image of the loading receptacle in response to receiving the identifier of the second medication container.

6. The method of claim 1, further comprising:
    providing for display of a reference image comprising an image of a reference medication unit at the device located remotely from the replenishment station.

7. The method of claim 6, further comprising:
    providing for display of the captured image on the device located remotely from the replenishment station; and
    receiving an approval of the replenishment process in response to the medication in the target quantity of medication matching the reference medication unit.

8. The method of claim 1, wherein causing an image to be captured of the loading receptacle comprising the target quantity of medication comprises causing a first image to be captured, the method further comprising:
    causing a second image to be captured of the loading receptacle comprising the target quantity of medication in response to determining that the first image captured is of relatively low quality.

9. The method of claim 1, wherein initiating a replenishment process comprises receiving an indication that the replenishment process is ready to begin at the replenishment station.

10. The method of claim 1, further comprising:
    providing an indication of a successfully completed replenishment process in response to receiving an approval of the replenishment process.

11. A computer program product comprising at least one non-transitory computer-readable storage medium having computer-executable program code instructions stored therein, the computer-executable program code instructions, when executed by a processor, are configured to:
    Initiate a replenishment process wherein a medication is identified that requires replenishment;
    provide an indication of the identified medication that requires replenishment;
    receive an identifier of a medication container containing a plurality of unit doses of a medication that is to be loaded into a loading receptacle;
    confirm that the identifier of the medication container corresponds to the identified medication, wherein an alert is generated in response to the identifier of the medication container does not correspond to the identified medication;
    receive an indication that a quantity of dispensed medication from the medication container in the loading receptacle has reached a target quantity for dispensing;
    cause an image to be captured of the loading receptacle comprising the target quantity of medication;
    provide the captured image to a device located remotely from the replenishment station; and
    receive an approval or rejection of the replenishment process in response to providing the captured image to a device located remotely from the replenishment station.

12. The computer program product of claim 11, further comprising program code instructions configured to:
    provide for display of the captured image of the loading receptacle comprising the target quantity of medication;
    provide for display of a reference image comprising an image of a reference medication unit, wherein the reference image comprises one or more of a distinctive color, shape, or indicia sufficient to distinguish a proper medication from an improper medication; and receive an approval or rejection of at least one stage of the replenishment process, in response to providing for the display of respective images.

13. The computer program product of claim 11, wherein a medication is identified that requires replenishment in response to an alert indicating an available quantity of the medication is below a threshold amount.

14. The computer program product of claim 11, wherein the identifier of a medication container containing a plurality of unit doses of a medication that is to be loaded into a receptacle is a first medication container, the computer program product further comprising program code instructions to:

receive an identifier of a second medication container containing a plurality of unit doses of a medication that is to be loaded into a loading receptacle in response to the target quantity of medication being greater than a quantity of medication from the first medication container being less than the target quantity; and confirm that the identifier of the second medication container corresponds to the identified medication, wherein an alert is generated in response to the identifier of the second medication container does not correspond to the identified medication.

15. The computer program product of claim 14, further comprising program code instructions to:

capture an image of the loading receptacle in response to receiving the identifier of the second medication container.

16. The computer program product of claim 11, further comprising program code instructions configured to:

provide for display of a reference image comprising an image of a reference medication unit at the device located remotely from the replenishment station.

17. The computer program product of claim 16, further comprising program code instructions configured to:

Provide for display of the captured image on the device located remotely from the replenishment station; and receive an approval of the replenishment process in response to the medication in the target quantity of medication matching the reference medication unit.

18. The computer program product of claim 11, wherein the program code instructions configured to cause an image to be captured of the loading receptacle comprising the target quantity of medication comprises program code instructions configured to cause a first image to be captured, the computer program product further comprising program code instructions configured to:

cause a second image to be captured of the loading receptacle comprising the target quantity of medication in response to determining that the first image captured is of relatively low quality.

19. The computer program product of claim 11, wherein the program code instructions configured to initiate a replenishment process comprises program code instructions configured to receive an indication that the replenishment process is ready to begin at the replenishment station.

20. A replenishment station comprising processing circuitry, at least one non-transitory memory, a user interface, and an image capture device, wherein the processing circuitry is configured to:

initiate a replenishment process wherein a medication is identified that requires replenishment;

provide an indication of the identified medication that requires replenishment via the user interface;

receive an identifier of a medication container containing a plurality of unit doses of a medication that is to be loaded into a loading receptacle;

confirm that the identifier of the medication container corresponds to the identified medication, wherein an alert is generated in response to the identifier of the medication container does not correspond to the identified medication;

receive an indication via the user interface that a quantity of dispensed medication from the medication container in the loading receptacle has reached a target quantity for dispensing;

cause an image to be captured by the image capture device of the loading receptacle comprising the target quantity of medication;

provide the captured image to a device located remotely from the replenishment station; and receive an approval or rejection of the replenishment process in response to providing the captured image to a device located remotely from the replenishment station.

* * * * *